US012454536B2

(12) United States Patent
Lai et al.

(10) Patent No.: US 12,454,536 B2
(45) Date of Patent: Oct. 28, 2025

(54) DEUTERATED 7-(3-(4-(2-([18F]FLUORO)ETHOXY)PHENYL) PROPYL)-2-(FURAN-2-YL)-7H- PYRAZOLO [4,3-E][1,2,4]TRIAZOLO[1,5-C]PYRIMIDINE-5-AMINE DERIVATIVES

(71) Applicants: HELMHOLTZ-ZENTRUM DRESDEN-ROSSENDORF E.V., Dresden (DE); ROTOP PHARMAKA GMBH, Dresden (DE)

(72) Inventors: Thu Hang Lai, Dresden (DE); Rodrigo Teodoro, Dresden (DE); Magali Toussaint, Dresden (DE); Daniel Gündel, Dresden (DE); Winnie Deuther-Conrad, Dresden (DE); Sladjana Dukic-Stefanovic, Dresden (DE); Susann Schröder, Dresden (DE); Rares-Petru Moldovan, Dresden (DE); Peter Brust, Dresden (DE)

(73) Assignees: HELMHOLTZ-ZENTRUM DRESDEN-ROSSENDORF E.V., Dresden (DE); ROTOP PHARMAKA GMBH, Dresden (DE)

( * ) Notice: Subject to any disclaimer, the term of this patent is extended or adjusted under 35 U.S.C. 154(b) by 978 days.

(21) Appl. No.: 17/620,848

(22) PCT Filed: Jun. 22, 2020

(86) PCT No.: PCT/EP2020/067343

§ 371 (c)(1),
(2) Date: Dec. 20, 2021

(87) PCT Pub. No.: WO2020/260196

PCT Pub. Date: Dec. 30, 2020

(65) Prior Publication Data

US 2023/0095104 A1 Mar. 30, 2023

(30) Foreign Application Priority Data

Jun. 24, 2019 (DE) ..................... 10 2019 116 986.0

(51) Int. Cl.
*C07D 487/14* (2006.01)

(52) U.S. Cl.
CPC ........ *C07D 487/14* (2013.01); *C07B 2200/05* (2013.01)

(58) Field of Classification Search
CPC ... C07D 487/14; C07B 2200/05; A61P 25/00; A61P 35/00
See application file for complete search history.

(56) References Cited

FOREIGN PATENT DOCUMENTS

| | | | |
|---|---|---|---|
| WO | 95/01356 | A1 | 1/1995 |
| WO | 97/05138 | A1 | 2/1997 |

(Continued)

OTHER PUBLICATIONS

Sukhninder Kaur and Monika Gupta, Glob J Pharmaceu Sci 1(4): GJPPS.MS.ID.555566 (2017) (Year: 2017).*

(Continued)

*Primary Examiner* — Clinton A Brooks
*Assistant Examiner* — Izabela Schmidt
(74) *Attorney, Agent, or Firm* — Maier & Maier, PLLC

(57) ABSTRACT

A compound of general formula I (I)

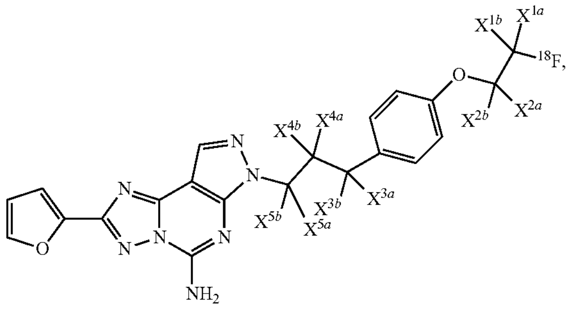

Residues $X^{1a}$, $X^{1b}$, $X^{2a}$, $X^{2b}$, $X^{3a}$, $X^{3b}$, $X^{4a}$, $X^{4b}$, $X^{5a}$, and $X^{5b}$ each independently are hydrogen or deuterium, with the (Continued)

provision that at least one of residues $X^{1a}$, $X^{1b}$, $X^{2a}$, $X^{2b}$, $X^{3a}$, $X^{3b}$, $X^{4a}$, $X^{4b}$, $X^{5a}$, and $X^{5b}$ is deuterium.

6 Claims, 1 Drawing Sheet

(56) References Cited

FOREIGN PATENT DOCUMENTS

| | | | | | |
|---|---|---|---|---|---|
| WO | 01/92264 | A1 | | 12/2001 | |
| WO | 03/048165 | A1 | | 6/2003 | |
| WO | 2005/044245 | A1 | | 5/2005 | |
| WO | WO-2012129381 | A1 | * | 9/2012 | ........... C07B 59/002 |

OTHER PUBLICATIONS

Khanapur et. al J. Med. Chem. 2014, 57, 6765-6780 (Year: 2014).*
Khanapur et al., Preclinical Evaluation and Quantification of 18F-Fluoroethyl and 18F-Fluoropropyl Analogs of SCH442416 as Radioligands for PET Imaging of the Adenosine A2A Receptor in Rat Brain, The Journal of Nuclear Medicine, vol. 58, No. 3, Mar. 2017, pp. 466-472.
Bhattacharjee et al., Striatal adenosine A2A receptor-mediated positron emission tomographic imaging in 6 hydroxydopamine-lesioned rats using [18 F]-MRS5425, Nuclear Medicine and Biology, vol. 38, 2011, pp. 897-906.
Hesk et al., Synthesis of 3H, 2H4, and 14C-MK 3814 (preladenant), Journal of Labeled Compounds and Radiopharmaceuticals, vol. 60, 2017, No. 4, pp. 194-199.
Khanapur et al., Development of [18F]-labeled Pyrazolo[4,3-e]-1,2,4-triazolo[1,5-c]pyrimidine (SCH442416) analogs for the imaging of cerebral adenosine A2A receptors with positron emission tomography, Journal of medicinal chemistry, vol. 57, 2014, H.15, pp. 6765-6780.
Buteau, Deuterated drugs: Unexpectedly nonobvious?, Journal of high technology law, vol. 10, 2009, No. 1, pp. 22-74.
Translation of Written Opinion of the International Searching Authority issued on Oct. 1, 2020 in corresponding International Application No. PCT/EP2020/067343; 6 pages.
Office Action issued on Jan. 14, 2020 in corresponding German Application No. 10 2019 116 986.0; 10 pages including partial machine generated English-language translation.
Office Action issued on Oct. 6, 2021 in corresponding German Application No. 10 2019 116 986.0; 12 pages including partial machine generated English-language translation.
Office Action issued on May 12, 2025, in corresponding European Application No. 20 734 882.2, 6 pages.

* cited by examiner

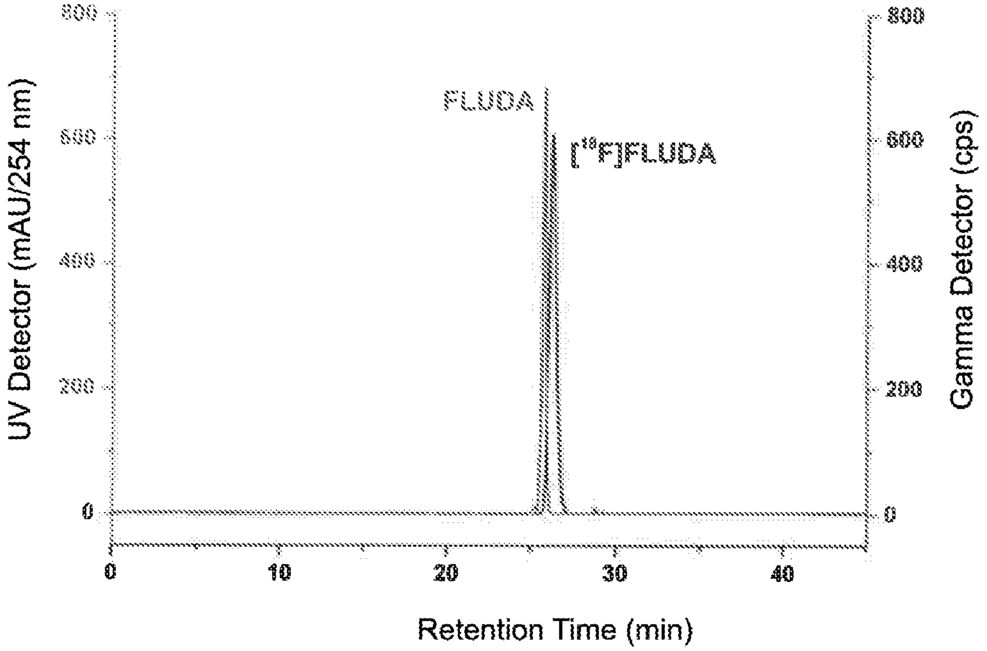
FLUDA
[18F]FLUDA
UV Detector (mAU/254 nm)
Gamma Detector (cps)
800
600
400
200
0
0
10
20
30
40
Retention Time (min)

DEUTERATED 7-(3-(4-(2-([18F]FLUORO)ETHOXY)PHENYL) PROPYL)-2-(FURAN-2-YL)-7H- PYRAZOLO [4,3-E][1,2,4]TRIAZOLO[1,5-C]PYRIMIDINE-5-AMINE DERIVATIVES

FIELD

The invention relates to deuterated 7-(3-(4-(2-([$^{18}$F] fluoro)ethoxy)phenyl)propyl)-2-(furan-2-yl)-7H-pyrazolo [4,3-e][1,2,4]triazolo[1,5-c]pyrimidine-5-amine derivatives and their use as a medicament. In particular it relates to the use of these derivatives as radiopharmaceuticals for nuclear-medical imaging of adenosine $A_{2A}$ receptors by means of positron emission tomography (PET).

BACKGROUND 2-(Furan-2-yl)-7H-pyrazolo[4,3-e][1,2,4]triazolo[1,5-c] pyrimidine-5-amine derivatives of the general formula B are known from WO1995/001356 A1, WO1997/005138 A1, WO2001/092264 A1, WO2003/048165 A1, and WO2005/044245 A1.

(B)

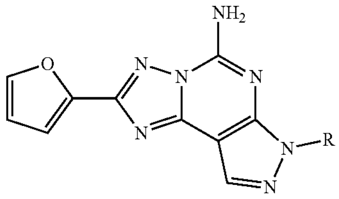

The derivatives are described as ligands for adenosine $A_{2A}$ receptors. They should therefore be suitable as therapeutic agents for treating diseases that are associated with adenosine $A_{2A}$ receptors.

Adenosine $A_{2A}$ receptors belong to the group of the G-protein coupled receptors (GPCRs) that mediate the effects of adenosine on various organ systems. In particular, adenosine $A_{2A}$ receptors couple to stimulatory $G_s$-proteins. The coupled $G_s$-proteins in turn activate adenylate cyclases and as a result induce the production of cAMP. A pharmacological blockage or induction of the adenosine $A_{2A}$ receptors therefore can have influence on various human diseases. However, the pharmacological influence by the administration of compounds that inhibit or stimulate $A_{2A}$ receptors on the one hand requires to know their effects as accurate as possible. On the other hand, it is desired to develop compounds that have the highest possible efficacy if diseases associated with changes of adenosine $A_{2A}$ receptors are to be diagnosed and treated. The efficacy is mainly determined by the binding strength (affinity) to the adenosine $A_{2A}$ receptor and the selectivity over other protein molecules.

Based on the 2-(furan-2-yl)-7H-pyrazolo[4,3-e][1,2,4]triazolo[1,5-c]pyrimidine-5-amine basic framework the selective $A_{2A}$ antagonist preladenant (Compound C) has been developed and was investigated in several clinical studies. Deuterated preladenant derivatives are known from WO2012/129381 A1. These compounds are said to be particularly suitable for the treatment of Parkinson's disease.

(C)

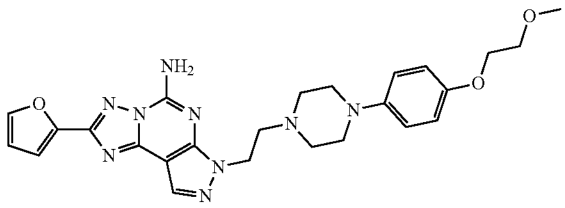

The compound 7-(3-(4-(2-fluoroethoxy)phenyl)propyl)-2-(furan-2-yl)-7H-pyrazolo[4,3-e][1,2,4]triazolo[1,5-c]pyrimidine-5-amine (D) has been published by Shinkre et al. (Bioorg. Med. Chem. Lett., 20, 2010). Starting from said compound the $^{18}$F-labeled compound D has been developed and for the first time pre-clinically investigated in rats in Bhattacharjee et al. (Nucl. Med. Biol., 38, 2011) and Khanapur et al. (J. Med. Chem., 57, 2014 and J. Nucl. Med. Chem, 58, 2017).

(D with Z = F or $^{18}$F)

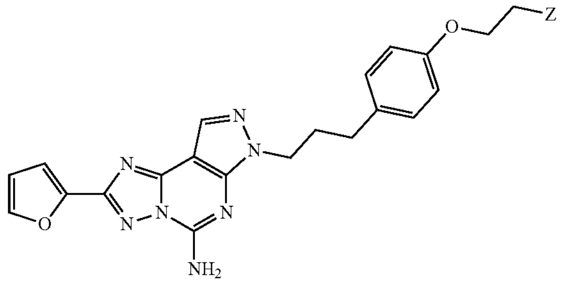

According to the prior art (Khanapur et al., J. Med. Chem., 57, 2014) the $^{18}$F-labeled compound D is prepared via a two-stage two-pot radiosynthesis with a radiochemical yield of 7±2% and a molar activity of 22±5% (n=18).

However, for a medical application of compound D higher radio-chemical yields and a higher molar activity are desired. The same applies to derivatives of compound D. Moreover, such derivatives should have a higher metabolic stability.

The problem of the invention is to overcome the drawbacks according to the prior art. In particular, there are provided 7-(3-(4-(2-([$^{18}$F]fluoro)ethoxy)phenyl)propyl)-2-(furan-2-yl)-7H-pyrazolo[4,3-e][1,2,4]triazolo[1,5-c]pyrimidine-5-amine derivatives that have a higher molar activity and a higher metabolic stability compared to compound D. In addition there is provided a method for the preparation of 7-(3-(4-(2-([$^{18}$F]fluoro)ethoxy)phenyl)propyl)-2-(furan-2-yl)-7H-pyrazolo[4,3-e][1,2,4]triazolo[1,5-c]pyrimidine-5-amine derivatives that permits their preparation with high radio-chemical yields.

SUMMARY

According to the invention there is provided a compound of general formula I:

(I)

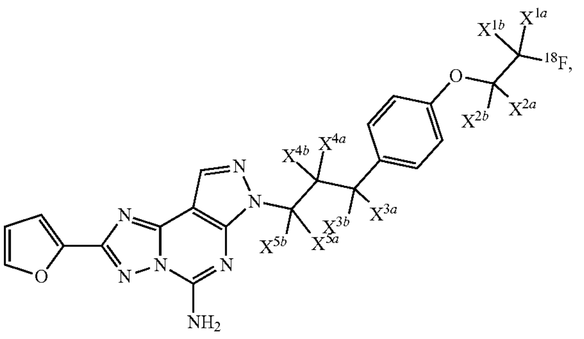

wherein the residues $X^{1a}$, $X^{1b}$, $X^{2a}$, $X^{2b}$, $X^{3a}$, $X^{3b}$, $X^{4a}$, $X^{4b}$, $X^{5a}$, and $X^{5b}$ each independently are hydrogen or deuterium, with the provision that at least one of the residues $X^{1a}$, $X^{1b}$, $X^{2a}$, $X^{2b}$, $X^{3a}$, $X^{3b}$, $X^{4a}$, $X^{4b}$, $X^{5a}$, and $X^{5b}$ is deuterium. In the following the specification "X" designates any residue of the residues $X^{1a}$, $X^{1b}$, $X^{2a}$, $X^{2b}$, $X^{3a}$, $X^{3b}$, $X^{4a}$, $X^{4b}$, $X^{5a}$, and $X^{5}$b.

It may be provided that the residues $X^{1a}$, $X^{1b}$, $X^{2a}$, and $X^{2b}$ each independently are hydrogen or deuterium and that the residues $X^{3a}$, $X^{3b}$, $X^{4a}$, $X^{4b}$, $X^{5a}$, and $X^{5b}$ each are hydrogen, wherein at least one of the residues $X^{1a}$, $X^{1b}$, $X^{2a}$, and $X^{2b}$ is deuterium.

It may further be provided that the residues $X^{1a}$ and $X^{1b}$ each are deuterium, the residues $X^{2a}$ and $X^{2b}$ each independently are hydrogen or deuterium, and the residues $X^{3a}$, $X^{3b}$, $X^{4a}$, $X^{4b}$, $X^{5a}$, and $X^{5b}$ each are hydrogen.

In a preferred embodiment it is provided that the residues $X^{1a}$, $X^{1b}$, $X^{2a}$, and $X^{2b}$ each are deuterium and the residues $X^{3a}$, $X^{3b}$, $X^{4a}$, $X^{4b}$, $X^{5a}$, and $X^{5b}$ each are hydrogen. In the following said compound is also referred to as $[^{18}F]$FLUDA and is shown below:

($[^{18}F]$FLUDA)

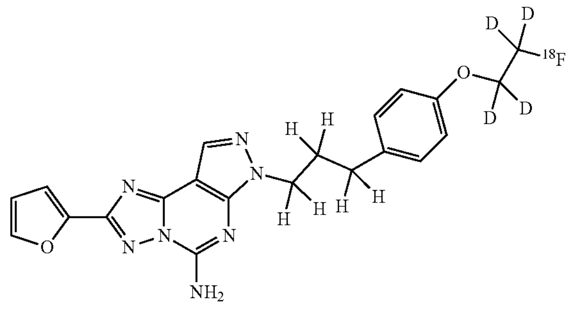

It turned out that the compounds of general formula I according to the invention represent ligands for adenosine $A_{2A}$ receptors. They can therefore be used to diagnose neurodegenerative diseases and/or oncological diseases. The oncological diseases may be neurooncological diseases. The compounds of general formula I according to the invention can therefore be used to diagnose cancer diseases and other hyper and/or dysproliferative diseases. In particular, cancer diseases comprise benign and malignant tumor diseases (neoplasms), especially tumor diseases of the lung, of the brain, of the spinal cord, of the prostate, of the bladder, of the kidney, of the oesophagus, of the stomach, of the pancreas, of the ovary, of the skeletal system. An example of a tumor disease of the lung is the non-small-cell lung carcinoma. Thus, the compounds of general formula I according to the invention can be used as a medicament, especially as a medicament for neurodegenerative diseases and/or oncological diseases. Also, a pharmaceutically acceptable salt of a compound of general formula I can be used as a medicament, especially as a medicament for neurodegenerative diseases and/or oncological diseases. In one embodiment the compounds of general formula I according to the invention can be used as a medicament for the diagnosis of a non-small-cell lung carcinoma. Also, a pharmaceutically acceptable salt of a compound of general formula I can be used as a medicament, especially as a medicament for the diagnosis of a nonsmall-cell lung carcinoma.

Moreover, the compounds according to the invention can be used to diagnose cardiovascular diseases. Thus, the compounds of general formula I according to the invention can be used as a medicament for cardiovascular diseases. Also, a pharmaceutically acceptable salt of a compound of general formula I can be used as a medicament for cardiovascular diseases.

Thus, according to the invention there is provided the use of a compound of general formula I as a medicament. Further provided is the use of a compound of general formula I as a medicament for the diagnosis of diseases in which an adenosine $A_{2A}$ receptor is involved. The medicament is a radiopharmaceutical. Preferably, the medicament is a radiopharmaceutical for the nuclear-medical imaging of adenosine $A_{2A}$ receptors by means of positron emission tomography (PET). Instead of a medicament containing a compound of general formula I according to the invention a pharmaceutically acceptable salt of said compound can be used.

According to the invention there is further provided a first method for the preparation of a compound of general formula IA:

(IA)

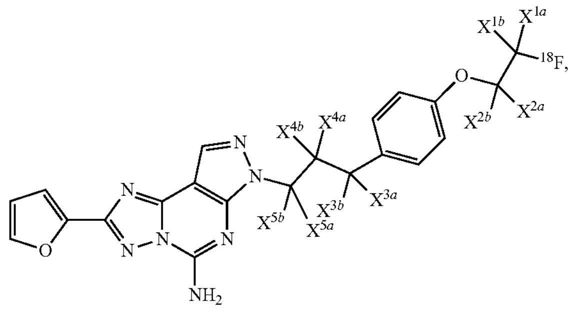

wherein the residues $X^{1a}$, $X^{1b}$, $X^{2a}$, $X^{2b}$, $X^{3a}$, $X^{3b}$, $X^{4a}$, $X^{4b}$, $X^{5a}$, and $X^{5b}$ each independently are hydrogen or deuterium, wherein a first precursor of general formula II (II)

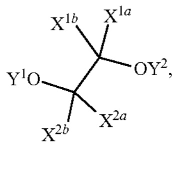

wherein the residues $X^{1a}$, $X^{1b}$, $X^{2a}$, and $X^{2b}$ have the meaning given in connection with formula IA and the residues $Y^1$ and $Y^2$ each independently are tosyl or mesyl, and a second precursor of formula III (III)

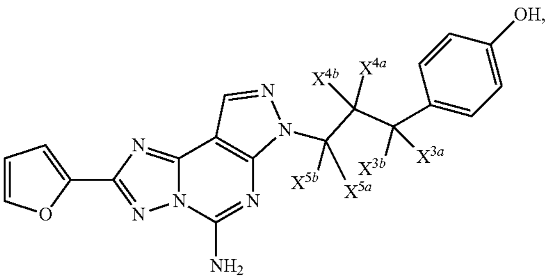

wherein the residues $X^{3a}$, $X^{3b}$, $X^{4a}$, $X^{4b}$, $X^{5a}$, and $X^{5b}$ have the meaning given in connection with formula IA, are reacted in a [$^{18}$F]fluoride-containing solution to obtain the compound of general formula IA. In the following the specification "Y" designates any residue of residues $Y^1$ and $Y^2$.

The compound of general formula I corresponds to the compound of general formula IA, apart from the fact that the compound of general formula IA necessarily has a residue X that is deuterium. In contrast to the compound of general formula I in the compound of general formula IA all the residues X can be hydrogen. In this case the compound of general formula IA is compound D known from the prior art in which Z is $^{18}$F. The method according to the invention is suitable for the preparation both of compound D and the deuterated derivatives of compound D in a one-pot method. The compounds of general formula I are deuterated derivatives of compound D.

The first method according to the invention preferably is a method for the preparation of a compound of general formula I. More preferably, the first method is used for the preparation of a compound of general formula IA in which at least one of residues $X^{1a}$, $X^{1b}$, $X^{2a}$, and $X^{2b}$ is deuterium and residues $X^{3a}$, $X^{3b}$, $X^{4a}$, $X^{4b}$, $X^{5a}$, and $X^5$b each are hydrogen. For the preparation of such a compound there is preferably used compound 1 as the second precursor:

(1)

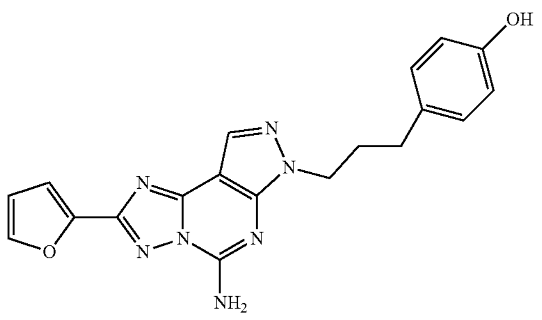

Compound 1 is a compound of general formula III in which $X^{3a}$, $X^{3b}$, $X^{4a}$, $X^{4b}$, $X^{5a}$, and $X^{5b}$ each are hydrogen. Compound 1 can be reacted with a compound of general formula II to a compound of general formula IB (IB)

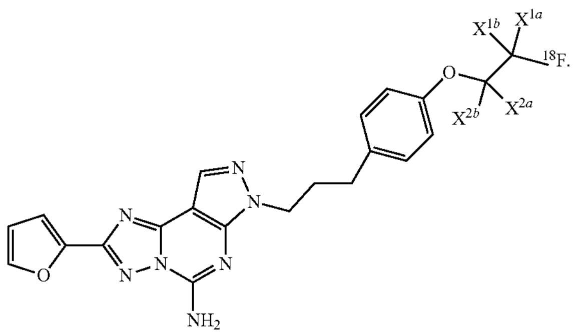

Formula IB corresponds to formula IA except that in formula IB residues $X^{3a}$, $X^{3b}$, $X^{4a}$, $X^{4b}$, $X^{1a}$, and $X^{5b}$ each are hydrogen. Especially preferred the first method according to the invention is a method for the preparation of [$^{18}$F] FLUDA.

Residues $Y^1$ and $Y^2$ each independently are tosyl or mesyl. Especially preferred residues $Y^1$ and $Y^2$ both are tosyl.

In one embodiment the first method according to the invention can comprise a first reaction step in which the first precursor is added to the [$^{18}$F]fluoride-containing solution and reacted there to a compound of general formula IV, as is shown in scheme 1 below.

Scheme 1

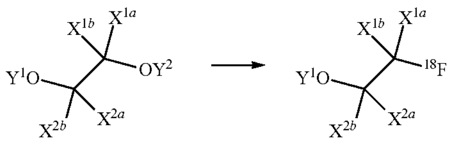

(II) (IV)

In formula II residues $X^{1a}$, $X^{1b}$, $X^{2a}$, and $X^{2b}$ have the meanings given in connection with formula IA and residues $Y^1$ and $Y^2$ have the meanings given above. In formula IV residues $X^{1a}$, $X^{1b}$, $X^{2a}$, $X^{2b}$, and $Y^1$ have the meanings given in connection with formula II. A compound of formula IV differs from a compound of formula II only in the nucleophilic substitution of residue $OY^2$ by [$^{18}$F]fluoride. In a second reaction step the compound of general formula IV is reacted with the second precursor to the compound of general formula IA, as shown in scheme 2.

Scheme 2

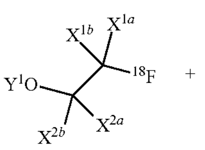

(IV)

-continued

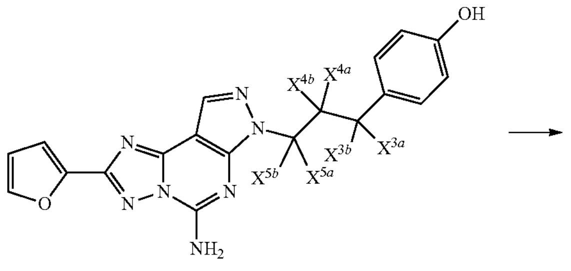

(III)

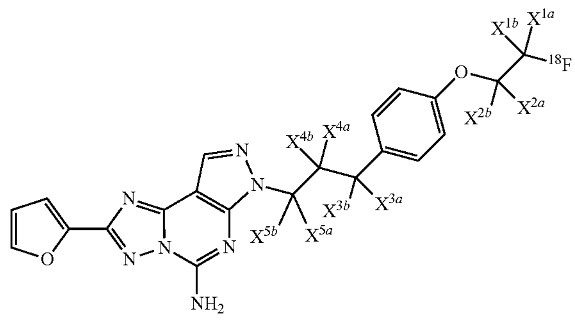

(IA)

Scheme 2A illustrates the reaction of a compound of general formula IV with compound 1 to a compound of general formula IB. Formula IB corresponds to formula IA except that in formula IB residues $X^{3a}$, $X^{3b}$, $X^{4a}$, $X^{4b}$, $X^{5a}$, and $X^{5b}$ each are hydrogen. [$^{18}$F]FLUDA is an example of a compound of general formula IB.

Scheme 2A

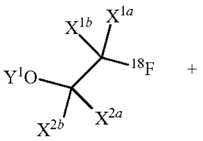

(IV)

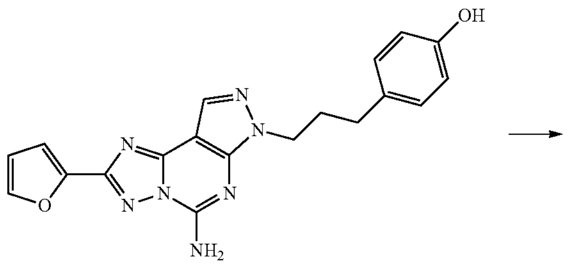

(1)

-continued

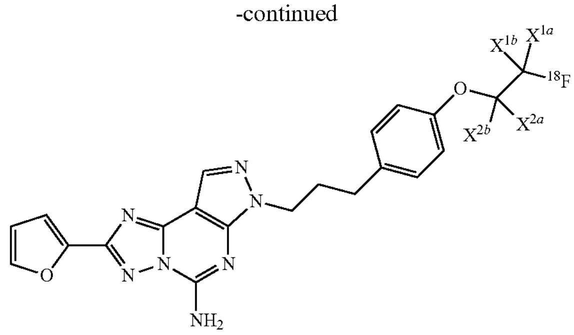

(IB)

The [$^{18}$F]fluoride anion can be prepared by means of known methods. For example, the [$^{18}$F]fluoride anion is prepared in the cyclotron by irradiating $H_2{}^{18}O$ enriched to at least 97% with protons of an energy of 9.6 MeV. The aqueous [$^{18}$F]fluoride solution obtained in this way can be fixed on an anion exchange cartridge (QMA) and eluted with the aid of an aqueous solution of a base, such as potassium carbonate, cesium carbonate, sodium hydride, or tetraalkylammonium hydrogen carbonate. Preferably, an aqueous solution of potassium carbonate is used as the base. The elution of the basic [$^{18}$F]fluoride solution takes place in a reaction vessel containing a phase transfer catalyst (PTC), such as crown ethers, quaternary ammonium salts, or alkaline or alkaline-earth salts. As the PTC there are preferably used a [2,2,2]-cryptand (Kryptofix® or K222), tetra-n-butylammonium-phosphate, -hydroxide, -oxalate, toluene sulfonate, or alternatively other crown ethers such as 18-crown-6. The [$^{18}$F]fluoride complex obtained in this way can be subjected to an azeotropic drying under vacuum. The organic solvent can be a non-protic, polar solvent such as acetonitrile (MeCN), dimethyl formamide (DMF), N,N-dimethyl acetamide (DMAA), N-methyl-2-pyrrolidone (NMP), dimethyl sulfoxide (DMSO), or mixtures thereof. Preferably, acetonitrile is used as the solvent. The azeotropic drying is preferably carried out under thermal reaction control in a closed reaction vessel at an elevated temperature. Preferably, the temperature is between 50 and 60° C. The azeotropic drying can also be carried out with the assistance of microwaves. For that, microwaves with a power of 50 to 150 W, preferably 65 to 85 W, and particularly 75 W can be used.

For carrying out the first reaction step the azeotropically dried [$^{18}$F]fluoride complex is preferably dissolved in an organic solvent. In this way, the [$^{18}$F]fluoride-containing solution is obtained. The organic solvent can be a non-protic, polar solvent such as acetonitrile (MeCN), dimethyl formamide (DMF), N,N-dimethyl acetamide (DMAA), N-methyl-2-pyrrolidone (NMP), dimethyl sulfoxide (DMSO), or mixtures thereof. Preferably, acetonitrile is used as the solvent. Then, the first precursor is added to this solution. Preferably, the first precursor beforehand is dissolved in an organic solvent. Said solvent is preferably the same solvent that is contained in the [$^{18}$F]fluoride-containing solution, i.e. acetonitrile. Then, the first precursor dissolved in the solvent is added to the [$^{18}$F]fluoride-containing solution.

Preferably, the first reaction step of the first method according to the invention is carried out at an increased temperature. Preferably, the temperature is between 80 and 110° C., particularly preferred is 90° C. Preferably, the first reaction step is carried out for a period of time of 5 to 15 min and particularly preferred 10 min. The first reaction step of the method according to the invention is preferably carried out at ambient pressure. The first reaction step is preferably carried out under agitation of the reaction mixture, for example under stirring.

In the first reaction step a compound of general formula IV is obtained in a reaction mixture. To this reaction mixture in a second reaction step of the method according to the invention the compound of general formula III that is the second precursor is added. The second reaction step of the first method according to the invention is preferably carried out at an increased temperature. The temperature is preferably between 100 and 140° C., particularly preferred 120° C. Preferably, the second reaction step is carried out for a period of time of 5 to 15 min and particularly preferred for 10 min. The second reaction step of the method according to the invention is preferably carried out at ambient pressure. The second reaction step is preferably carried out under agitation of the reaction mixture, for example under stirring.

It may be provided that the second precursor is subjected to a pretreatment before it is added to the reaction mixture containing the compound of general formula IV. In this case the pretreated second precursor is added to said reaction mixture. The pretreatment can comprise the treatment of the second precursor with a base that serves for deprotonation of the phenol group of the second precursor. In the following, said base is also referred to as activating base. For that, the second precursor is contacted with the activating base in an organic solvent. Preferably, said solvent is the same solvent that is contained in the [$^{18}$F]fluoride-containing solution as the solvent, i.e. acetonitrile. Then, the second precursor dissolved in the solvent is added to the reaction mixture.

The pretreatment of the second precursor is preferably carried out at an increased temperature. Preferably, the temperature is between 80 and 110° C., particularly preferred 90° C. Preferably, the pretreatment is carried out for a period of time of 5 to 15 min and particularly preferred for 10 min. Preferably, the pretreatment is carried out at ambient pressure. Preferably, the pretreatment is carried out under agitation of the reaction mixture, for example under stirring. The concentration of the activating base is preferably between 35 and 45% by weight with respect to the solution containing the second precursor and the phase transfer catalyst, particularly preferred 40% by weight. In another embodiment the concentration of the activating base with respect to the solution containing the second precursor and the phase transfer catalyst can be between 1 and 10% by weight, preferably 2 and 8% by weight, and particularly preferred 5% by weight.

The activating base can have a cation of general formula $N^+(R^1R^2R^3R^4)$, wherein $R^1$, $R^2$, $R^3$, and $R^4$ are the same or different and each are unsubstituted or substituted $C_1$-$C_6$ alkyl. Preferably, $R^1$, $R^2$, $R^3$, and $R^4$ each are unsubstituted $C_1$-$C_6$ alkyl, more preferably propyl, butyl, or pentyl, particularly preferred each n-butyl. It may be provided that the activating base has an anion selected from the group comprising hydroxy, hydrogen carbonate, hydrogen sulfate, oxalate, phosphate, and toluene sulfonate. Hydroxy is highly preferred. In the following, an activating base having the cation tetra-n-butyl-ammonium is also referred to as TBA. A particularly preferred activating base is tetra-n-butyl-ammonium hydroxide (TBAOH). In the activating base the cation of general formula $N^+(R^1R^2R^3R^4)$ and the anion can be present in a stoichiometric ratio.

The first method according to the invention is a two-stage one-pot method. In the present invention a one-pot method is understood to be a method in which the first reaction step and the second reaction step are carried out in the same reaction vessel. It is therefore suitable to use the same solvent both for the first reaction step and the second reaction step.

The first method according to the invention permits the preparation of 7-(3-(4-(2-[$^{18}$F]fluoroethoxy)phenyl)propyl)-2-(furan-2-yl)-7H-pyrazolo-[4,3-e][1,2,4]-triazolo[1,5-c]pyrimidine-5-amine that is not deuterated by suitable precursors. Moreover, it permits the preparation of the deuterated 7-(3-(4-(2-[$^{18}$F]fluoroethoxy)phenyl)propyl)-2-(furan-2-yl)-7H-pyrazolo-[4,3-e][1,2,4]-triazolo[1,5-c]pyrimidine-5-amine derivatives of general formula I according to the invention by suitable precursors. Thus, it permits the use of the deuterated 7-(3-(4-(2-[$^{18}$F]fluoroethoxy)phenyl)propyl)-2-(furan-2-yl)-7H-pyrazolo[4,3-e][1,2,4]-triazolo[1,5-c]pyrimidine-5-amine derivatives of general formula I according to the invention as radiotracers. The compounds of general formula I according to the invention can therefore be used as highly affine and selective adenosine $A_{2A}$ radiopharmaceuticals. The $^{18}$F-labeled radiotracers of general formula I that can be obtained by means of the invention can be used for in-vitro and in-vivo investigations on the expression of adenosine $A_{2A}$ receptors in organisms by positron emission tomography (PET). These investigations permit to gain more precise knowledge about the effect of a reference compound and in addition to the radiopharmaceutical get access or assessments to further medicaments and make an important contribution to their evaluation, respectively.

According to the invention there is further provided the use of a compound of general formula II (II)

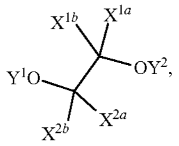

wherein residues $X^{1a}$, $X^{1b}$, $X^{2a}$, and $X^{2b}$ each independently are hydrogen or deuterium and residues $Y^1$ and $Y^2$ each independently are tosyl or mesyl, for the preparation of a compound of general formula IA, (IA)

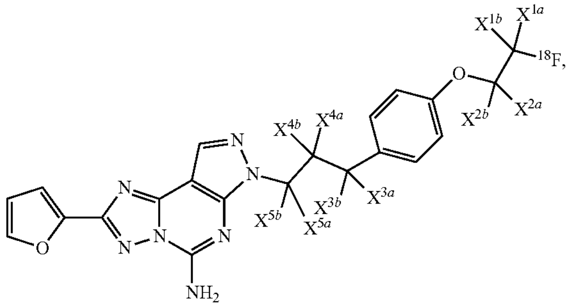

wherein residues $X^{1a}$, $X^{1b}$, $X^{2a}$, $X^{2b}$, $X^{3a}$, $X^{3b}$, $X^{4a}$, $X^{4b}$, $X^{5a}$, and $X^{5b}$ have the meanings given in connection with formula I. For the preparation of a compound of general formula IA the compound of general formula II as the first precursor is reacted with a compound of general formula III as the second precursor. Details going with it have been explained above in context with the method according to the invention. Reference is made to said explanations.

The use according to the invention particularly can provide the use of a compound of general formula II for the preparation of a compound of general formula IB. For the preparation of a compound of general formula IB the compound of general formula II as the first precursor is reacted with compound 1 as the second precursor.

A preferred compound of general formula II is compound 2 (ethane-1,2-diyl-$d_4$-bis(4-methylbenzene sulfonate)) as shown below.

(2)

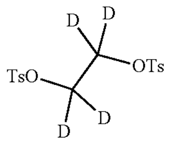

Compound 2 can be used for the preparation of [$^{18}$F]FLUDA. For the preparation of [$^{18}$F]FLUDA compound 2 is preferably reacted with compound 1.

By the development of a two-stage one-pot radiosynthesis the invention permits both higher radio-chemical yields and molar activities of compounds of general formula IA, including compound [$^{18}$F]D and deuterated 7-(3-(4-(2-[$^{18}$F]fluoroethoxy)phenyl)propyl)-2-(furan-2-yl)-7H-pyrazolo[4,3-e][1,2,4]triazolo[1,5-c]pyrimidine-5-amine derivatives of general formula I. The compounds of general formula I exhibit a significantly higher metabolic stability compared to the known $^{18}$F-labeled compound D. This concerns in particular [$^{18}$F]FLUDA.

The invention therefore differs from the prior art in particular by the two-stage one-pot radiosynthesis of deuterated 7-(3-(4-(2-[$^{18}$F]fluoroethoxy)phenyl)propyl)-2-(furan-2-yl)-7H-pyrazolo[4,3-e][1,2,4]-triazolo[1,5-c]pyrimidine-5-amine derivatives of general formula I and the subsequent use as radiotracers for the nuclear-medical imaging of adenosine $A_{2A}$ receptors by means of positron emission tomography (PET). The compounds of general formula I have a high affinity and selectivity over adenosine $A_{2A}$ receptors. That's why they are particularly suitable as radiopharmaceuticals for the nuclear-medical imaging of adenosine $A_{2A}$ receptors by means of PET.

According to the invention further provided is a second method for the preparation of a compound of general formula IA:

(IA)

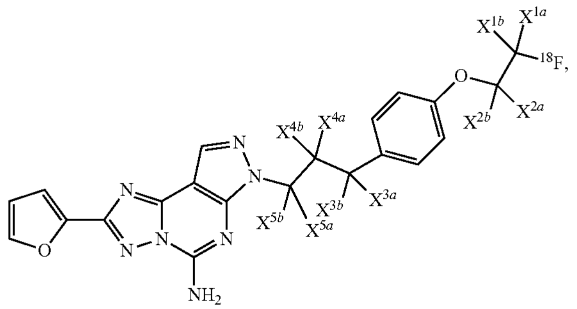

wherein residues $X^{1a}$, $X^{1b}$, $X^{2a}$, $X^{2b}$, $X^{3a}$, $X^{3b}$, $X^{4a}$, $X^{4b}$, $X^{5a}$, and $X^{5b}$ each independently are hydrogen or deuterium, wherein a precursor of general formula V (V)

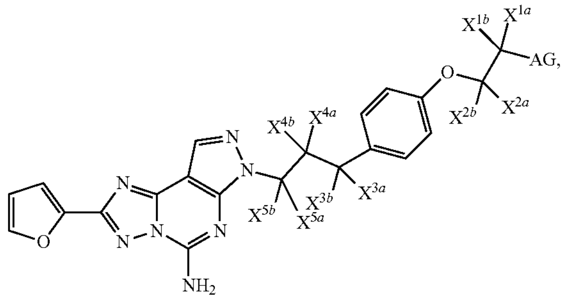

wherein residues $X^{1a}$, $X^{1b}$, $X^{2a}$, $X^{2b}$, $X^{3a}$, $X^{3b}$, $X^{4a}$, $X^{4b}$, $X^{5a}$, and $X^{5b}$ have the meaning given in connection with formula IA and AG is a leaving group selected from the group consisting of a sulfonate, chlorine, bromine, and iodine, is reacted to a compound of general formula IA in a [$^{18}$F]fluoride-containing solution.

The second method according to the invention preferably is a method for the preparation of a compound of general formula I. More preferably, the second method is used for the preparation of a compound of general formula IA in which at least one of residues $X^{1a}$, $X^{1b}$, $X^{2a}$, and $X^{2b}$ is deuterium and residues $X^{3a}$, $X^{3b}$, $X^{4a}$, $X^{4b}$, $X^{5a}$, and $X^{5b}$ each are hydrogen. For the preparation of such a compound a compound of general formula VA is used:

(VA)

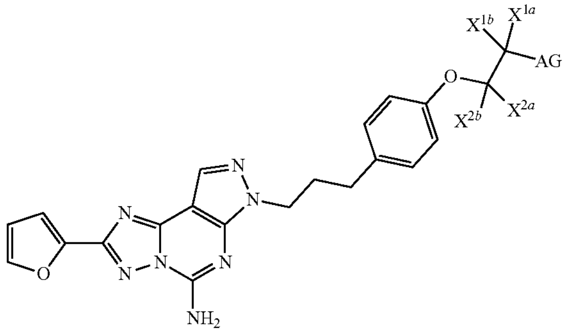

Compound VA is a compound of general formula V in which $X^{3a}$, $X^{3b}$, $X^{4a}$, $X^{4b}$, $X^{5a}$ and $X^{5b}$ each are hydrogen. Compound VA can be reacted to a compound of general formula IB (IB)

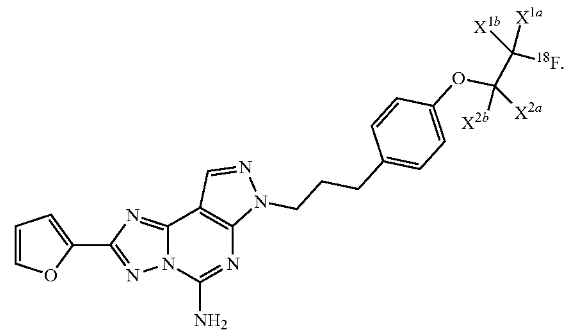

Particularly preferred the second according to the invention is a method for the preparation of [$^{18}$F]FLUDA.

In the compounds of general formulae V and VA AG preferably is a sulfonate. The term "sulfonate" is understood to be an $R^S$—$SO_2$—O group. For example, $R^S$ may be a branched or unbranched, substitute or unsubstituted $C_1$-$C_6$ alkyl group, an aryl group, or an alkylaryl group. Preferably, $R^S$ is $CH_3$—, $CF_3$—, $CH_3C_6H_4$—, or $NO_2$—$C_6H_4$—. For example, the sulfonate can be selected from the group consisting of a toluene sulfonic acid ester group, a methyl sulfonic acid ester group, a trifluormethyl sulfonic acid ester group, and a p-nitrobenzene sulfonic acid ester group. A toluene sulfonic acid ester group is understood to be a —OTs group when Ts is tosyl. A methyl sulfonic acid ester group is understood to be a —OMs group wherein Ms is mesyl. A trifluoromethyl sulfonic acid ester group is understood to be $CF_3$—$SO_2$—O—. A p-nitrobenzene sulfonic acid ester group is understood to be a $NO_2$—$C_6H_4$—$SO_2$—O group. Preferably, AG is —OMs or —OTs. Particularly preferred AG is —OTs. It may be provided that the sulfonate is not a dibromobenzene sulfonic acid ester group ($(Br)_2$—$C_6H_4$—$SO_2$—O-group), particularly not a 3,4-dibromobenzene sulfonic acid ester group.

Scheme 6 illustrates the preparation of a compound of general formula IA by means of the second method according to the invention.

Scheme 6

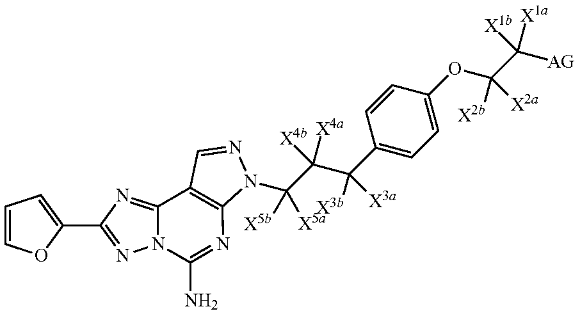

(V)

-continued

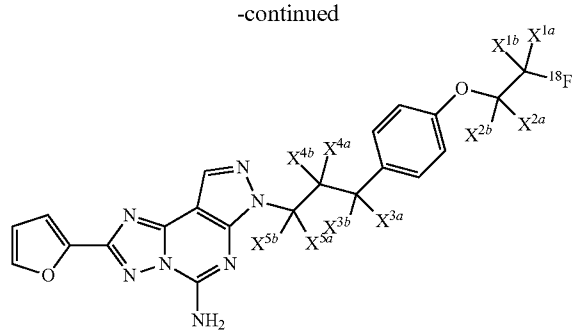

(IA)

Scheme 6A illustrates the preparation of a compound of general formula IB by means of the second method according to the invention starting from compound VA. The compound of formula IB differs from a compound of formula VA only by the nucleophilic, aliphatic substitution of the group AG by [$^{18}$F]fluoride.

Scheme 6A

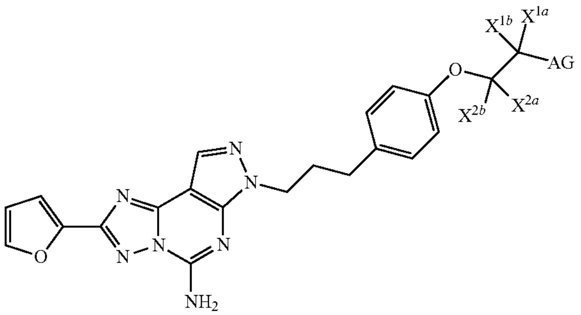

(VA)

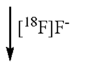

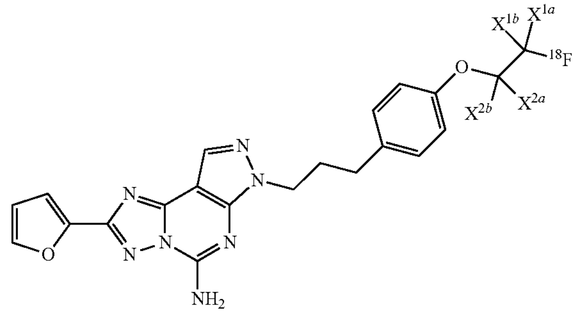

(IB)

The preparation of the [$^{18}$F]fluoride anion can be done in the same manner as has been described in the context of the first method according to the invention.

For carrying out the second method according to the invention the azeotropically dried [$^{18}$F]fluoride complex is preferably dissolved in an organic solvent. In this way, the [$^{18}$F]fluoride-containing solution is obtained. The organic solvent may be a non-protic, polar solvent such as acetonitrile (MeCN), dimethyl formamide (DMF), N,N-dimethyl acetamide (DMAA), N-methyl-2-pyrrolidone (NMP), dimethyl sulfoxide (DMSO), or mixtures thereof. Preferably, acetonitrile is used as the solvent. Then, the compound of general formula V is added to said solution. Preferably, the compound of general formula V beforehand is dissolved in an organic solvent. Said solvent preferably is the same solvent contained as solvent in the [$^{18}$F]fluoride-containing solution, i.e. acetonitrile. Then, the compound of general formula V dissolved in the solvent is added to the [$^{18}$F]fluoride-containing solution.

The second method according to the invention is preferably carried out at an increased temperature. The temperature is preferably between 80 and 110° C., particularly preferred 90° C. Preferably, the first reaction step is carried out for a period of time of 5 to 15 min and particularly preferred 10 min. The first reaction step of the method according to the invention is preferably carried out at ambient pressure. The first reaction step is preferably carried out under agitation of the reaction mixture, for example under stirring.

The compound of general formula V can be prepared by reacting a compound of general formula III with a compound of general formula VII, as is shown in Scheme 7.

Scheme 7

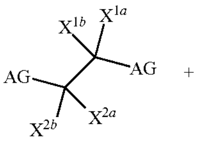

(VII)

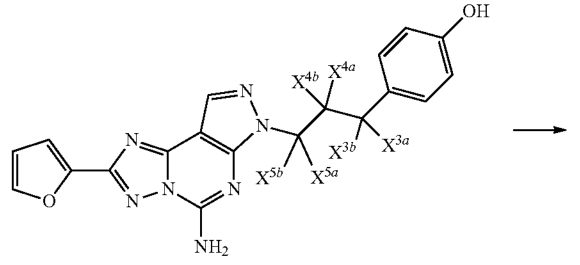

(III)

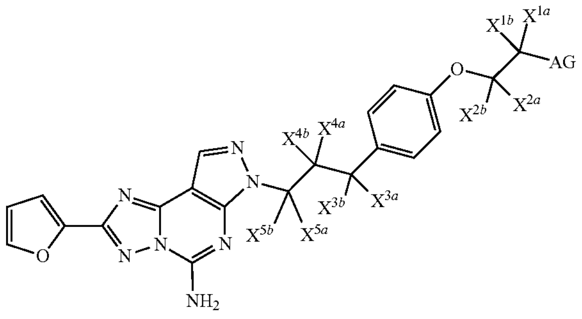

(V)

In the compound of general formula VII the groups AG each independently have the meanings given in connection with the compound of general formula V wherein both groups AG may be the same or different. Preferably, both groups each are a sulfonate, preferably each —OTs.

Scheme 7A illustrates the preparation of a compound of general formula VA using compound 1.

Scheme 7A

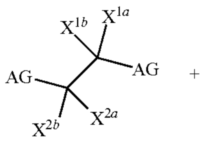

(VII)

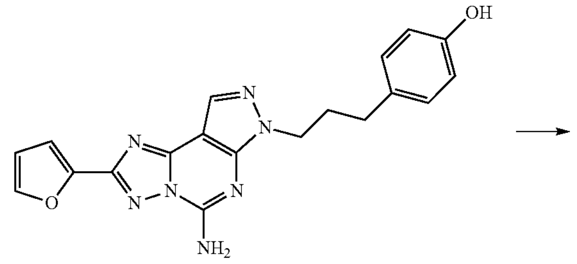

(1)

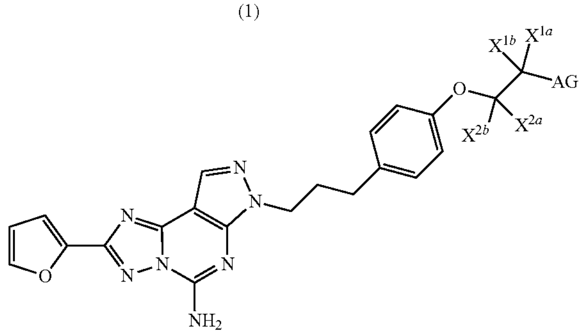

(VA)

Compound V is preferably prepared using an organic solvent. The organic solvent may be a non-protic, polar solvent such as acetonitrile (MeCN), dimethyl formamide (DMF), N,N-dimethyl acetamide (DMAA), N-methyl-2-pyrrolidone (NMP), dimethyl sulfoxide (DMSO), or mixtures thereof. Preferably, acetonitrile is used as the solvent. The reaction is preferably carried out at an increased temperature. The temperature is preferably between 100 and 140° C., particularly preferred 120° C. Preferably, the reaction is carried out for a period of time of 5 to 15 min and particularly preferred 10 min. The reaction is preferably carried out at ambient pressure. The reaction is preferably carried out under agitation of the reaction mixture, for example under stirring.

It may be provided that the compound of general formula III is subjected to a pretreatment as is described in connection with the pretreatment of the second precursor in the first method according to the invention. For that, an activating base described there can be employed.

The second method according to the invention is a one-stage method for the preparation of a compound of general formula IA.

The second method according to the invention permits the preparation of 7-(3-(4-(2-[$^{18}$F]fluoroethoxy)phenyl)propyl)-2-(furan-2-yl)-7H-pyrazolo-[4,3-e][1,2,4]-triazolo[1,5-c]pyrimidine-5-amine that is not deuterated. Moreover, it permits the preparation of the deuterated 7-(3-(4-(2-[$^{18}$F]fluoroethoxy)phenyl)propyl)-2-(furan-2-yl)-7H-pyrazolo-[4,3-e][1,2,4]-triazolo[1,5-c]pyrimidine-5-amine derivatives of general formula I according to the invention. It therefore permits the use of the deuterated 7-(3-(4-(2-[$^{18}$F]fluoroethoxy)phenyl)propyl)-2-(furan-2-yl)-7H-pyrazolo[4, 3-e][1,2,4]-triazolo[1,5-c]pyrimidine-5-amine derivatives of general formula I according to the invention as radiotracers.

According to the invention there is additionally provided a third method for the preparation of a compound of general formula I according to the invention:

(I)

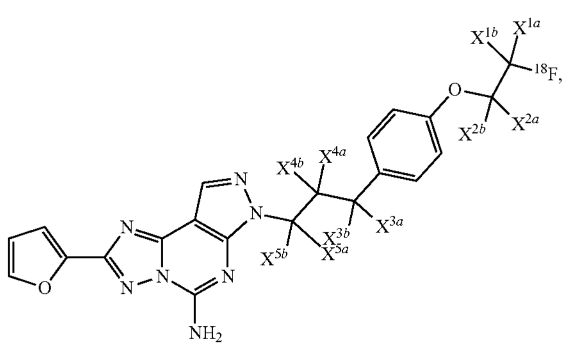

wherein residues $X^{1a}$, $X^{1b}$, $X^{2a}$, $X^{2b}$, $X^{3a}$, $X^{3b}$, $X^{4a}$, $X^{4b}$, $X^{5a}$, and $X^{5b}$ each independently are hydrogen or deuterium, with the provision that at least one of residues $X^{1a}$, $X^{1b}$, $X^{2a}$, $X^{2b}$, $X^{3a}$, $X^{3b}$, $X^{4a}$, $X^{4b}$, $X^{5a}$, and $X^{5b}$ is deuterium, wherein a compound of general formula VII (VII)

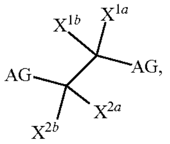

wherein residues $X^{1a}$, $X^{1b}$, $X^{2a}$, and $X^{2b}$ have the meaning given in connection with formula I and the two residues AG each independently are a leaving group selected from the group consisting of a sulfonate, chlorine, bromine, and iodine, and a precursor of formula III (III)

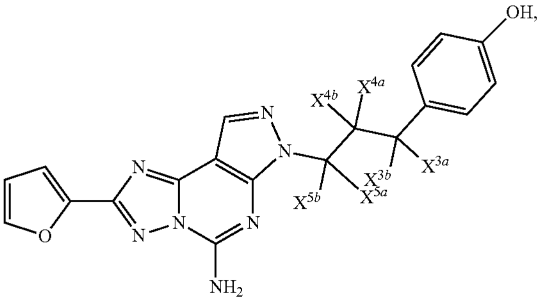

wherein residues $X^{3a}$, $X^{3b}$, $X^{4a}$, $X^{4b}$, $X^{5a}$, and $X^{5b}$ have the meaning given in connection with formula I are reacted in a [$^{18}$F]fluoride-containing solution to obtain the compound of general formula I.

The third method according to the invention corresponds to the first method according to the invention except that the compound of general formula VII is used instead of the first precursor of general formula II. In the first reaction step the compound of general formula VII can be added to the [$^{18}$F]fluoride-containing solution and there reacted to a compound of general formula VIII, as shown in scheme 9 below.

Scheme 9

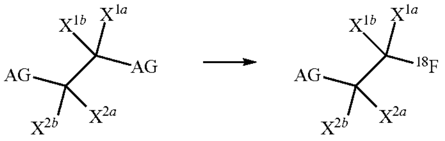

(VII) (VIII)

In formula VII residues $X^{1a}$, $X^{1b}$, $X^{2a}$, and $X^{2b}$ have the meanings given in connection with formula IA and both groups AG have the meanings given above. In formula VIII residues $X^{1a}$, $X^{1b}$, $X^{2a}$, $X^{2b}$, and $Y^1$ have the meanings given in connection with formula VII. A compound of formula VIII differs from a compound of formula VII only in the nucleophilic aliphatic substitution of one of the two groups AG by [$^{18}$F]fluoride. In the second reaction step the compound of general formula VIII is reacted with the precursor of general formula III to the compound of general formula IA, as shown in scheme 10.

Scheme 10

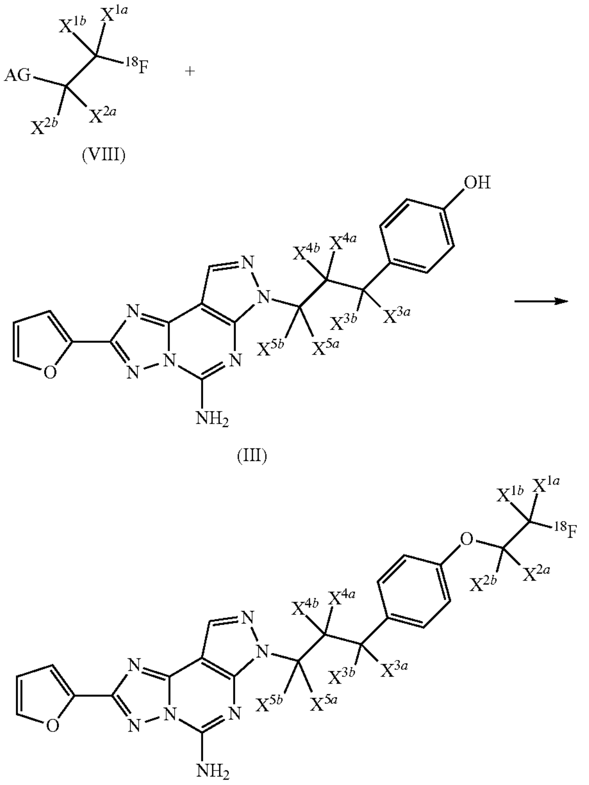

(VIII)

(III)

(IA)

Scheme 10A illustrates the reaction of a compound of general formula VIII with compound 1 to a compound of general formula IB.

Scheme 10A

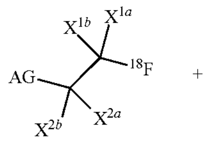

(VIII)

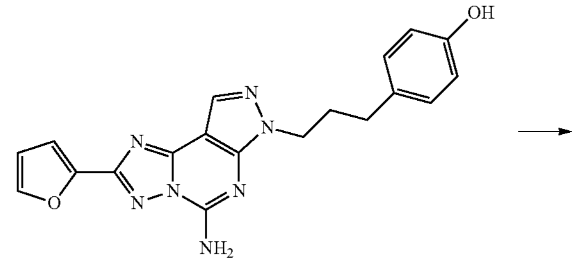

(1)

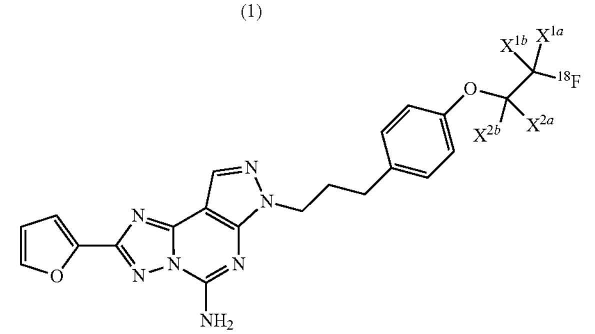

(IB)

The first precursor of general formula II used in the first method is a preferred compound of general formula VII, in which both groups AG each are —OTs or —OMs. The first method according to the invention therefore can be considered as a preferred embodiment of the third method according to the invention. Details on the first method according to the invention therefore can be found in the description of the first method according to the invention. Here, the compound of general formula VII takes the place of the first precursor. The compound of general formula III used in the third method according to the invention in connection with the first method according to the invention is referred to as the second precursor.

In the compound of general formula VII both groups AG preferably are a sulfonate, as has been described in connection with the second method according to the invention. Preferably, AG is —OMs or —OTs. Particularly preferred AG is —OTs.

Preferably, the third method is used for the preparation of a compound of general formula I, in which at least one of residues $X^{1a}$, $X^{1b}$, $X^{2a}$, and $X^{2b}$ is deuterium and residues $X^{3a}$, $X^{3b}$, $X^{4a}$, $X^{4b}$, $X^{5a}$, and $X^{5b}$ each are hydrogen.

The third method according to the invention can be carried out as a two-stage one-pot method. Here, the first reaction step and the second reaction step are carried out in the same reaction vessel. It is therefore suitable to use the same solvent both for the first reaction step and the second reaction step.

The third method according to the invention permits the preparation of 7-(3-(4-(2-[$^{18}$F]fluoroethoxy)phenyl)propyl)-2-(furan-2-yl)-7H-pyrazolo-[4,3-e][1,2,4]-triazolo[1,5-c]pyrimidine-5-amine that is not deuterated. Moreover, it permits the preparation of the deuterated 7-(3-(4-(2-[$^{18}$F]fluoroethoxy)phenyl)propyl)-2-(furan-2-yl)-7H-pyrazolo-[4,3-e][1,2,4]-triazolo[1,5-c]pyrimidine-5-amine derivatives of general formula I according to the invention. It therefore permits the use of the deuterated 7-(3-(4-(2-[$^{18}$F]fluoroethoxy)phenyl)propyl)-2-(furan-2-yl)-7H-pyrazolo[4,3-e][1,2,4]-triazolo[1,5-c]pyrimidine-5-amine derivatives of general formula I according to the invention as radiotracers.

It is known that hydrogen is a polyisotopic element. In the preparation of compound D known from the prior art therefore small amounts of deuterated isotopologues can be obtained. However, the proportion of the deuterated isotopologues is small because it is determined by the natural frequency of deuterium. In the present invention each atom that is not explicitly mentioned as a specific isotope is a stable isotope. Unless otherwise stated a residue referred to as hydrogen or H is understood to be a residue having hydrogen in its natural abundance ratio. Unless otherwise stated a residue referred to as deuterium or D is understood to be a residue having deuterium in a frequency that is at least 3000 times greater than the natural frequency of deuterium. By assuming a natural frequency of deuterium of 0.015% a 3000 times higher frequency means a deuteration of 45%. The term "isotopologue" denotes molecules that only differ in their isotopic composition. They have the same chemical formula and the same binding ratios between the atoms, but differ in at least one atom having another number of neutrons.

The ratio between the frequency of an isotope in a compound and the natural frequency of the isotope is referred to as "isotope enrichment factor". As described above, the isotope enrichment factor for each atom denoted as deuterium shall be at least 3000 (45% deuteration with a residue referred to as deuterium). The isotope enrichment factor can be at least 3500 (52.5% deuteration), at least 4000 (60% deuteration), at least 4500 (67.5% deuteration), at least 5000 (75% deuteration), at least 5500 (82.5% deuteration), at least 6000 (90% deuteration), at least 6333.3 (95% deuteration), at least 6466.7 (97% deuteration), at least 6600 (99% deuteration), or at least 6633.3 (99.5% deuteration).

A compound that according to the invention should have at least one deuterium atom may be considered as a group of isotopologues. The proportion of the isotopologues that form a compound can vary. A compound that according to the invention should have at least one deuterium atom contains smaller amounts of isotopologues that have hydrogen atoms instead of one or more of the given deuterium atoms. The relative amount of said isotopologues should be less than 55% of the compound based on the compound. It may be provided that the relative amount of these isotopologues is less than 50%, less than 47.5%, less than 40%, less than 32.5%, less than 25%, less than 17.5%, less than 10%, less than 5%, less than 3%, less than 1%, or less than 0.5%.

BRIEF DESCRIPTION OF THE FIGURE

In the following the invention is explained in detail with the help of examples not intended to limit the invention with reference to the drawing. Here FIG. 1 shows HPLC chromatograms to detect the product unit of [$^{18}$F]FLUDA.

DETAILED DESCRIPTION

In scheme 3 there is shown the synthesis of compound 5 for the subsequent use as a starting substance for the reaction with compound 5 represented in scheme 4 for the synthesis of the non-radioactive ligand FLUDA having an affinity of $K_i(hA_{2A})$=0.609 nM and $K_i(hA_1)$=767 nM. Further tests, taking into account the above data, showed an affinity for FLUDA of $K_i(hA_{2A})$=0.74±0.26 nM (n=3) and $K_i(hA_1)$>1 μM (n=3).

Scheme 3

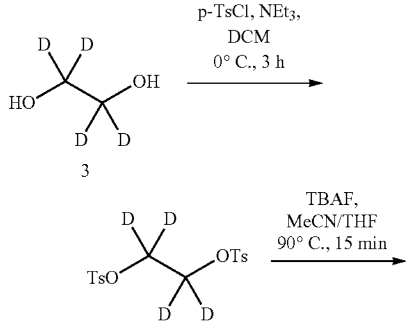

3 4 5

Scheme 4

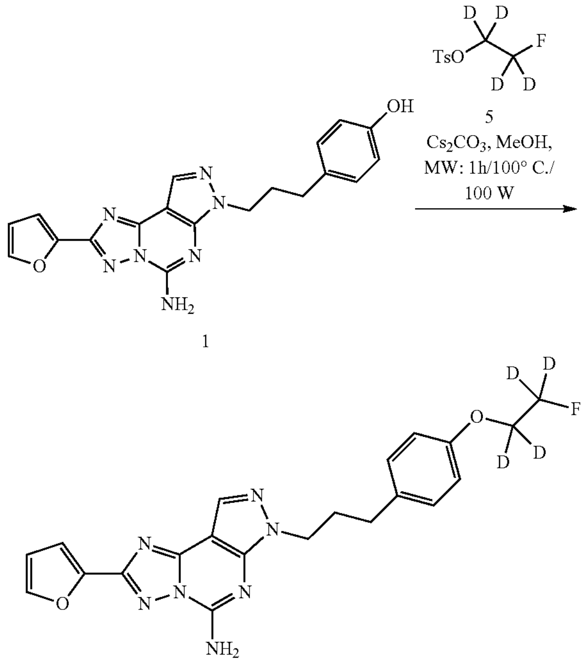

5 1 FLUDA

Example 1

Synthesis of Ethan-1,2-diyl-$d_4$ bis(4-methylbenzene sulfonate) (4)

The synthesis was in analogy to the specification described by Hesk et al. (*J. Labelled Comp. Radiopharm.*, 60, 2017): The ethane-$d_4$-1,2-diol (1 g; 15.1 mmol) was dissolved in dichloromethane (DCM; 15 ml) and mixed with triethylamine ($NEt_3$; 3.8 ml; 27.2 mmol). Subsequently, para-toluene sulfonic acid chloride (p-TsCl; 4.3 g; 22.7 mmol) was added at 0° C. under argon atmosphere. The reaction mixture was stirred at 0° C. until complete reaction conversion. Then, processing with water and saturated sodium chloride solution took place. After drying the organic phase with magnesium sulfate and removal of the solvent the raw product was washed with ethanol for several times. A colorless solid was obtained as the product (3.8 g; 68%).

$^1$H-NMR (400 MHz, $CDCl_3$): δ=7.72 (d, J=8.4 Hz, 4H), 7.33 (d, J=8.0 Hz, 4H), 2.45 (s, 2H); $^{13}$C-NMR (101 MHz, $CDCl_3$): δ=145.40 (2C), 132.48 (2C), 130.08 (4C), 128.07 (4C), 21.79 (2C).

Example 2

Synthesis of 2-fluoroethyl-1,1,2,2-$d_4$ 4-methylbenzene sulfonate (5)

Ethane-1,2-diyl-$d_4$-bis(4-methylbenzene sulfonate) (4, 520 mg; 1.39 mmol) was dissolved in acetonitrile (10 ml) and mixed with tetrabutylammonium fluoride (TBAF, 1M in tetrahydrofuran (THF); 2.22 ml; 2.22 mmol) under argon atmosphere. The reaction mixture was stirred for 15 min at 90° C. After removal of the solvent the residue was dissolved with ethyl acetate (EtOAc) and an aqueous processing with water and saturated sodium chloride solution took place. After drying the organic phase with magnesium sulfate and removal of the solvent the raw product was purified by means of flash chromatography (gradient n-hexane/EtOAc 4:1→3:1→2:1). A colorless oil was obtained as the product (110 mg, 36%).

$^1$H-NMR (400 MHz, $CDCl_3$): δ=7.81 (d, J=8.3 Hz, 2H), 7.36 (d, J=8.0 Hz, 2H), 2.45 (s, 3H); $^{19}$F-NMR (377 MHz, $CDCl_3$): δ=−226.57 (s); $^{13}$C-NMR (101 MHz, $CDCl_3$): δ=145.28, 132.83, 130.07 (2C), 128.10 (2C) 21.79.

Example 3

Synthesis of 7-(3-(4-(2-(fluoro)ethoxy-1,1,2,2-$d_4$) phenyl)propyl)-2-(furan-2-yl)-7H-pyrazolo[4,3-e][1,2,4]triazolo[1,5-c]pyrimidine-5-amine (FLUDA)

The synthesis of FLUDA took place in a microwave-assisted reaction of 4-(3-(5-amino-2-(furan-2-yl)-7H-pyrazolo[4,3-e][1,2,4]triazolo[1,5-c]pyrimidine-7-yl)propyl) phenol (1, 50.7 mg; 0.135 mmol) and 2-fluoroethyl-1,1,2,2-$d_4$-4-methylbenzene sulfonate (5; 90 mg; 0.405 mmol) with cesium carbonate (132 mg, 0.405 mmol) in methanol (MeOH; 2.5 ml) at 1 hr/100° C./100 W. In scheme 4 the assistance by microwaves is shown with the abbreviation "MW". After removal of the solvent the residue was dissolved with ethyl acetate (EtOAc) and aqueous processing with water and saturated sodium chloride solution took place. After drying the organic phase with magnesium sulfate and removal of the solvent the raw product was purified by means of flash chromatography (gradient $CH_2Cl_2$/MeOH 100:1→100:2→100:3 and gradient EtOAc/petroleum ether 3:1→4:1→5:1). A colorless oil was obtained as the product (110 mg, 36%).

$^1$H-NMR (400 MHz, DMSO-$d_6$): δ=8.16 (s, 1H, 10), 8.06 (s, $NH_2$), 7.94 (dd, J=0.9, 1.8 Hz, 1H), 7.23 (dd, J=0.8, 3.4 Hz, 1H), 7.13 (d, J=8.7 Hz, 2H), 6.86 (d, J=8.6 Hz, 2), 6.73 (dd, J=1.8, 3.3 Hz, 1H), 4.25 (t, J=6.9 Hz, 2H), 2.54 (t, J=7.6 Hz, 2H), 2.11 (p, J=7.2 Hz, 2H); $^{19}$F-NMR (376 MHz, DMSO-$d_6$): δ=5.09 (s); $^{13}$C-NMR (101 MHz, DMSO-$d_6$): δ=156.38, 155.33, 148.70, 148.37, 146.25, 145.52, 145.06, 133.31, 131.28, 129.35 (2C), 114.34 (2C), 112.22, 112.10, 95.72, 46.06, 31.26, 30.90.

In scheme 5 there is shown the synthesis of [$^{18}$F]FLUDA using compound 2 as the first precursor and compound 1 as the second precursor.

Scheme 5

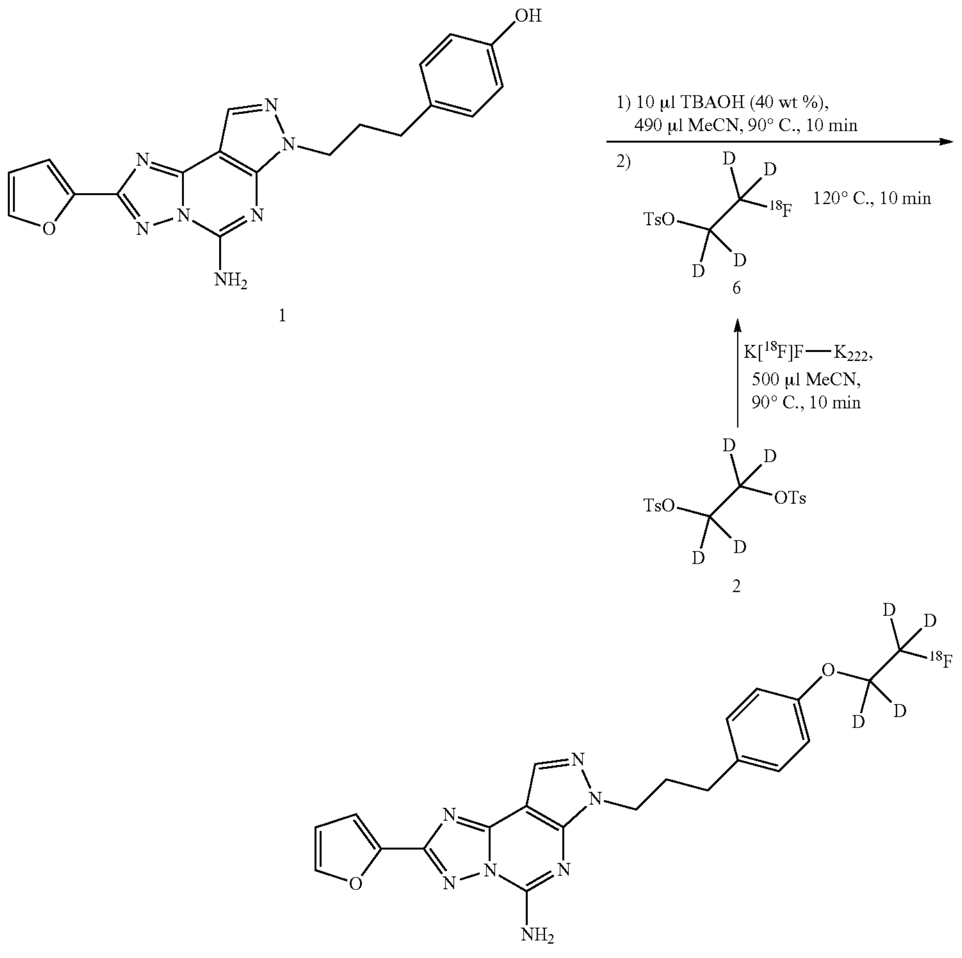

1 6 2

[18F]FLUDA

Specifications 1) and 2) in scheme 5 refer to the reaction of the second precursor 1. This is subjected to a pre-treatment that is marked with 1) and subsequently reacted with compound 6 what is marked with 2).

Example 4

Manual Synthesis of 7-(3-(4-(2-([$^{18}$F]fluoro)ethoxy-1,1,2,2-d$_4$)phenyl)propyl)-2-(furan-2-yl)-7H-pyrazolo[4,3-e][1,2,4]triazolo[1,5-c]pyrimidine-5-amine ([$^{18}$F]FLUDA)

For the preparation of [$^{18}$F]FLUDA the aqueous [$^{18}$F] fluoride (2-3 GBq) obtained after irradiation was added to 1 ml of water, fixed on an anion exchange cartridge (QMA) and eluted with an aqueous $K_2CO_3$ solution (1.8 mg in 300 μl of water) in a solution of 1 ml of MeCN and Kryptofix ($K_{222}$, 5.6 mg). The azeotropic drying of the complex was microwave-assisted (power cycling, 75 W, 50-60° C., argon stream) under vacuum. The [$^{18}$F]F/$K_{222}$/$K^+$ complex formed was dissolved in 400 μl of MeCN and mixed with compound 2 (3 mg) that is dissolved in MeCN (100 μl) and serves as the first precursor. Subsequently, the reaction mixture was stirred at 90° C. for 10 min. To determine the marking yield an aliquot was taken and analyzed by radio-TLC (81±8%, n=7) and radio-HPLC (67±4%, n=7).

Thereafter, compound 1 (3 mg) that was dissolved in MeCN (490 μl) and pretreated with TBAOH (10 μl, 40% by weight) at 90° C. for 10 min and serves as the first precursor was added to the reaction mixture and stirred at 120° C. for 10 min. To determine the marking yield an aliquot was taken and analyzed by radio-TLC (48±7%, n=6) and radio-HPLC (39±3%, n=6). Purification and isolation of the radiotracer [$^{18}$F]FLUDA took place by means of semi-preparative RP-HPLC (column: ReproSilPur 120 C18-AQ, 250×20 mm, 5 m; eluent: 58% of MeCN/20 mM of $NH_4OAc_{aq.}$; flow: 7 ml/min). The collected product fraction was diluted with water, sorbed on a Sep-Pak© C18 Plus cartridge and eluted with ethanol (1.5 ml). Subsequently, the solvent was removed under heating in the argon stream and formulated in 0.9% salt solution (10% of ethanol, v/v). The product [$^{18}$F]FLUDA was isolated within a synthesis time of ca. 102 min and analyzed by radio-HPLC and radio-TLC, wherein the identity of the product was confirmed by co-injection of the reference compound (FIG. 1). [$^{18}$F]FLUDA was obtained in a radio-chemical yield of 19±3% (EOB, n=9), with a radio-chemical purity of >99% and with a molar activity of 94±14 GBq/mol (EOS, n=7).

FIG. 1 shows the UV and radio-HPLC chromatograms of the formulated radiotracer [$^{18}$F]FLUDA with co-injection of the reference compound of 7-(3-(4-(2-(fluoro)ethoxy-1,1,2, 2-$d_4$)phenyl)propyl)-2-(furan-2-yl)-7H-pyrazolo[4,3-e][1,2,4]triazolo[1,5-c]pyrimidine-5-amine (FLUDA) for confirmation of identity (column: ReproSil-Pur C18-AQ, 250×4.6 mm, 5 m; eluent: 10-90-10% of MeCN/20 mM of $NH_4OAc$; flow: 1 ml/min).

Example 4A

Example 4 was repeated several times. As a result a molar activity of 72-180 GBq/mol (EOS) was obtained for [$^{18}$F]FLUDA.

Example 5

Automated Synthesis of 7-(3-(4-(2-([$^{18}$F]fluoro)ethoxy-1,1,2,2-$d_4$)phenyl)propyl)-2-(furan-2-yl)-7H-pyrazolo[4,3-e][1,2,4]triazolo[1,5-c]pyrimidine-5-amine ([$^{18}$F]FLUDA)

The automated radiosynthesis of [$^{18}$F]FLUDA for clinical employment can be carried out routinely in a commercial automatic synthesizer, preferably Tracerlab Fx2n by General Electrics by GE or Synchron R & D EVO III by Elysia-Raytest GmbH. Here, the two-stage one-pot synthesis takes place in analogy to example 4. [$^{18}$F]FLUDA is obtained within a synthesis time of ca. 110 min in a radio-chemical yield of 10±1% (EOB, n=2), with a radio-chemical purity of 99% and a molar activity of ca. 70 GBq/mol (EOS, initial activity: 3.4 GBq).

Example 5A

Example 5 was repeated several times. By taking into account the results of example 5 [$^{18}$F]FLUDA was obtained in a radio-chemical yield of 9±1% (EOB, n=9), with a radio-chemical purity of 99% and a molar activity of 69-333 GBq/mol (EOS, initial activity: 3-13 GBq).

Example 6

Study of the Properties of [$^{18}$F]FLUDA

[$^{18}$F]FLUDA has shown to be stable in a sodium chloride, PBS, n-octanol solution and in porcine plasma at 37° C. for one hour (PBS=phosphate buffered salt solution). Using the conventional "Shake-flask" method a log $D_{74}$=2.01±0.07 (n=3) has been established.

[$^{18}$F]FLUDA had an affinity of $K_d$=4.04±0.90 (n=3) and a $B_{max}$ of 556±143 fmol/mg (n=5). In the in-vivo metabolite study in female CD-1 mice after 15 min p.i. in the brain 93% (radio-HPLC, n=3, extraction yield 98%) and in the plasma 79% (radio-HPLC, n=3, extraction yield 83%) of intact radiotracers have been detected. The in-vitro autoradiography study in brain slices of the mice showed a selective enrichment of the radiotracer [$^{18}$F]FLUDA in the desired target region (striatum) and also a change of the radiotracer by means of $A_{2A}$-selective ligands. PET studies in healthy CD-1 mice showed a cerebral uptake of SUV=0.8 (striatum, 15 min p.i., n=3).

Example 6A

Example 6 was repeated several times. By taking into account the results of example 6 the following values have been established: in the brain 100% (radio-HPLC, n=3, extraction yield 98%) and in the plasma 82% (radio-HPLC, n=3, extraction yield 83%) of intact radiotracers.

Comparison Example 1

Study of the Properties of 7-(3-(4-(2-([$^{18}$F]fluoro)ethoxy)phenyl)propyl)-2-(furan-2-yl)-7H-pyrazolo[4,3-e][1,2,4]triazolo[1,5-c]pyrimidine-5-amine ([$^{18}$F]D)

The properties of compound [$^{18}$F]D have been determined in the same manner as described in example 6. Compound [$^{18}$F]D had affinities of $K_i(hA_{2A})$=0.06 (n=4) and $K_i(hA_1)$=203 nM (n=4). Furthermore, an affinity of $K_d$=4.69±1.17 (n=3) has been determined. In an in-vivo metabolite study in female CD-1 mice after 15 min p.i. in the brain 68% (radio-HPLC, n=3, extraction yield 97%) and in the plasma 70% (radio-HPLC, n=3, extraction yield 85%) of intact radiotracers have been detected.

Comparison Example 1A

Comparison example 1 was repeated. The following values have been established: in the brain 71% (radio-HPLC, n=1, extraction yield 98%) and in the plasma 41% (radio-HPLC, n=1, extraction yield 84%) of intact radiotracers.

Example 7

Synthesis of 7-(3-(4-(2-([$^{18}$F]fluoro)ethoxy-1,1,2,2-$d_4$)phenyl)propyl)-2-(furan-2-yl)-7H-pyrazolo[4,3-e][1,2,4]triazolo[1,5-c]pyrimidine-5-amine ([$^{18}$F]FLUDA)

In scheme 8 there is shown the synthesis of [$^{18}$F]FLUDA according to the second method according to the invention.

Scheme 8

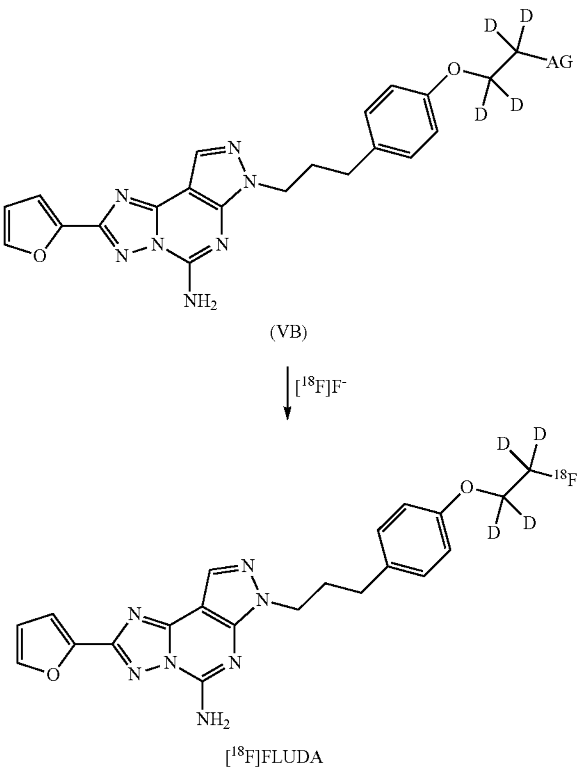

The compound of general formula VB is a compound of general formula V in which residues $X^{1a}$, $X^{1b}$, $X^{2a}$, and $X^{2b}$ each are deuterium, residues $X^{3a}$, $X^{3b}$, $X^{4a}$, $X^{4b}$, $X^{5a}$, and $X^{5b}$ each are hydrogen, and AG has the meaning given in connection with general formula V.

Example 8

Synthesis of 7-(3-(4-(2-([$^{18}$F]fluoro)ethoxy-1,1,2,2-$d_4$)phenyl)propyl)-2-(furan-2-yl)-7H-pyrazolo[4,3-e][1,2,4]triazolo[1,5-c]pyrimidine-5-amine ([$^{18}$F]FLUDA)

In scheme 11 there is shown the synthesis of [$^{18}$F]FLUDA according to the third method according to the invention.

Scheme 11

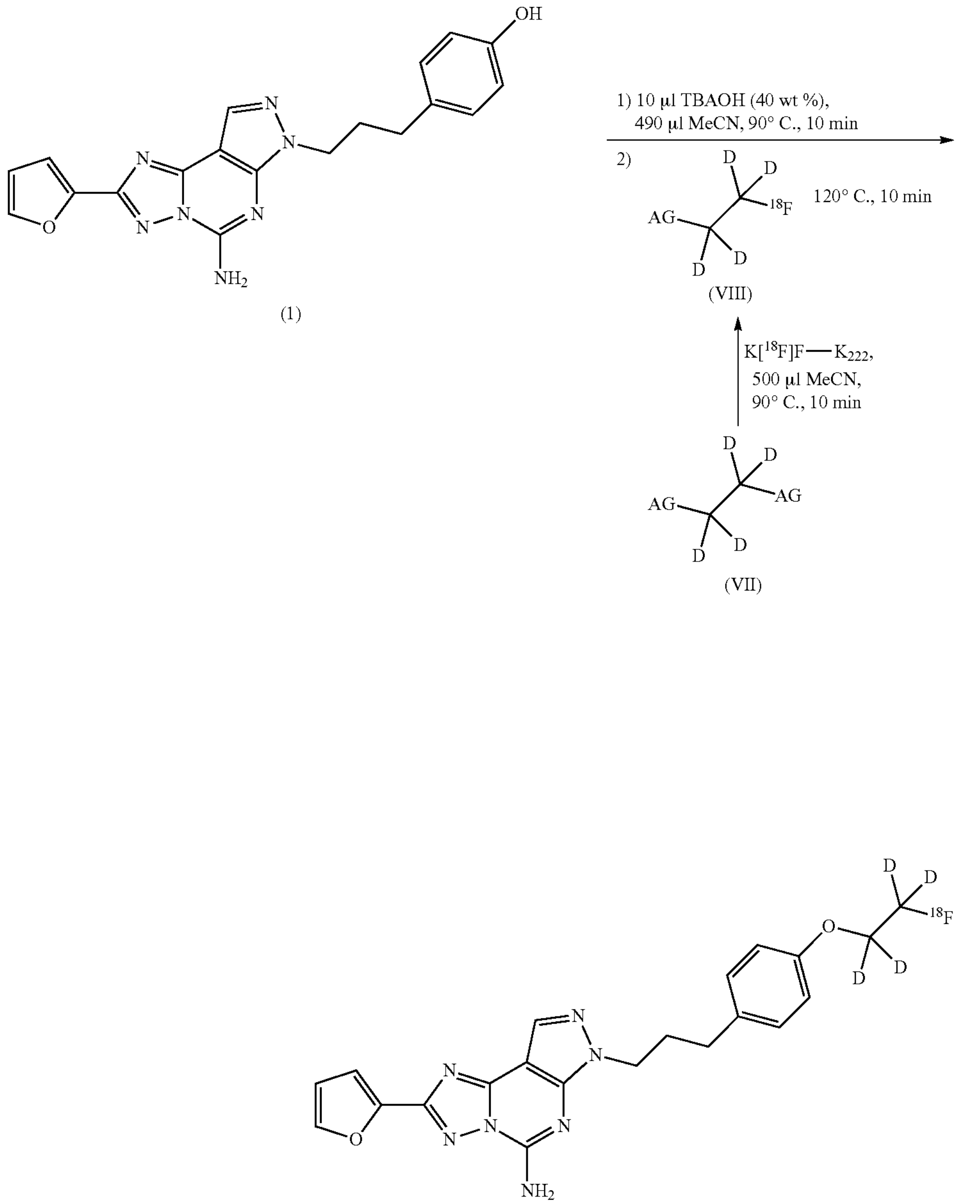

(1) (VIII) (VII) [$^{18}$F]FLUDA

The synthesis can be carried out as described in example 4.

The invention claimed is:

1. A compound of general formula I (V)

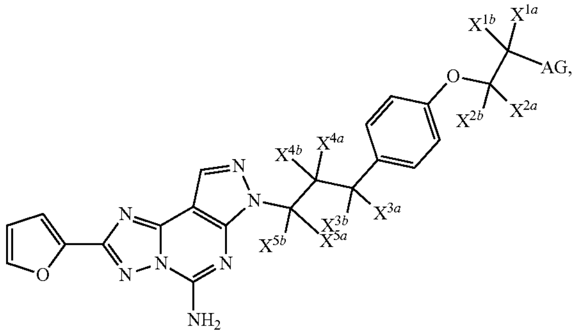

wherein residues $X^{1a}$, $X^{1b}$, $X^{2a}$, and $X^{2b}$ each are deuterium and residues $X^{3a}$, $X^{3b}$, $X^{4a}$, $X^{4b}$, $X^{5a}$, and $X^{5b}$ each are hydrogen.

2. The compound according to claim 1, wherein each of the residues $X^{1a}$, $X^{1b}$, $X^{2a}$, and $X^{2b}$ has an isotope enrichment factor of at least 3500.

3. The compound according to claim 1 for use as a medicament.

4. The compound according to claim 1 for use as a medicament for the diagnosis of diseases in which an adenosine $A_{2A}$ receptor is involved.

5. The compound according to claim 1, wherein the compound is suitable as a radiopharmaceutical for the nuclear-medical imaging of adenosine $A_{2A}$ receptors by means of positron emission tomography (PET).

6. A medicament containing a compound according to claim 1 or a pharmaceutically acceptable salt thereof.

* * * * *